United States Patent [19]
Archer

[11] Patent Number: 5,683,434
[45] Date of Patent: Nov. 4, 1997

[54] MICROSTRIP EMI SHUNT FOR AN IMPLANTABLE MEDICAL DEVICE

[75] Inventor: Stephen Thomas Archer, Sunnyvale, Calif.

[73] Assignee: Pacesetter, Inc., Sunnyvale, Calif.

[21] Appl. No.: 759,652

[22] Filed: Dec. 6, 1996

[51] Int. Cl.$^6$ .................................................. A61N 1/372
[52] U.S. Cl. .................................................. 607/36
[58] Field of Search .......................... 607/2, 9, 36–38, 607/63; 128/901, 908; 333/12, 182, 204

[56] References Cited

U.S. PATENT DOCUMENTS

| | | |
|---|---|---|
| 4,091,818 | 5/1978 | Brownlee et al. . |
| 4,934,366 | 6/1990 | Truex et al. . |
| 5,197,468 | 3/1993 | Proctor et al. . |

*Primary Examiner*—William E. Kamm
*Assistant Examiner*—George R. Evanisko
*Attorney, Agent, or Firm*—Steven M. Mitchell

[57] ABSTRACT

A microstrip EMI shunt for an implantable medical device (e.g., an ICD) which includes a microstrip transmission line secured to an interior surface of a housing of the device, the microstrip transmission line having a first end secured to a connector wire which is electrically coupled to internal electronics of the device, and a second end which is open-circuited. The microstrip transmission line has a length $n\lambda/4$, where $\lambda$ is the wavelength of EMI (in the microstrip medium) having a selected frequency f which is desired to be shunted, and n is an odd integer $\geq 1$. In operation, EMI of the frequency f is shunted via the microstrip transmission line prior to reaching the internal electronics of the device. Additional microstrip transmission lines having appropriately chosen lengths to shunt EMI of different frequencies can also be provided.

17 Claims, 1 Drawing Sheet

MICROSTRIP EMI SHUNT FOR AN IMPLANTABLE MEDICAL DEVICE

BACKGROUND OF THE INVENTION

The present invention relates generally to implantable medical devices, and more particularly, to a microstrip EMI shunt for implantable medical devices such as pacemakers and implantable cardioverter-defibrillators (ICDs).

Exemplary implantable medical devices include implantable cardiac stimulation devices, bladder stimulators, bone growth stimulators, cerebellar stimulators, deep brain stimulators, diaphragm pacers, peripheral nerve stimulators, peroneal nerve stimulators, scoliotis stimulators, and spinal cord stimulators. The majority of implantable medical devices work by delivering electrical stimuli to excitable tissue such as nerve or muscle tissue, in order to induce a desired physiological response. The present invention will be described herein in connection with implantable cardiac stimulation devices, although it will be readily apparent to those skilled in the pertinent art that it will also have utility with respect to many of the other types of implantable medical devices.

Various types of implantable cardiac stimulation devices are presently available for delivering various types of cardiac stimulation therapy. The two most common types which are in widespread use are pacemakers and ICDs. Pacemakers generally produce relatively low voltage pacing pulses which are delivered to the patient's heart through low voltage, "bipolar" pacing leads, generally across spaced-apart ring and tip electrodes which are of opposite polarity. These pacing pulses assist the natural pacing function of the heart in order to treat bradycardia. Contemporary ICDs are capable of delivering tiered therapy, e.g., anti-bradycardia pacing therapy, anti-tachycardia pacing (ATP) therapy, cardioversion therapy, and defibrillation therapy.

In general, an ICD continuously monitors the heart activity of the patient in whom the device is implanted by analyzing an electrical signal, known as an electrogram (EGM), detected by endocardial sensing electrodes positioned in the right ventricular apex and/or right atrium of the patient's heart and affixed to leads which are plugged into connector ports provided in a header attached to the housing of the ICD. The leads are secured in place within the connector ports of the header by means of setscrews which are tightened down onto lead connector pins of the leads via transversely disposed setscrew cavities provided in the header and in electrical connector blocks disposed about a distal end portion of the connector ports. The leads are electrically coupled to the internal electronics of the ICD by means of connector wires which are connected between the connector blocks and the internal electronics via ceramic feedthroughs.

The internal electronics of the ICD includes sense amplifiers for amplifying the analog EGM detected by the sensing electrodes, EGM waveform digitization circuitry for digitizing the analog EGM, a microprocessor and associated peripheral ICs which analyze the digitized EGM in accordance with a detection or diagnostic algorithm implemented by software stored in the microprocessor, one or more batteries for supplying the power for operating the device, a pair of series-connected high-voltage capacitors, and pulse generator circuitry for appropriately charging and discharging the high-voltage capacitors for delivery of the appropriate cardiac therapy. The sense amplifiers, EGM waveform digitization circuitry, microprocessor and associated peripheral ICs, batteries, capacitors, pulse generator circuitry, and other active components of ICDs are contained in the housing, which is constructed of titanium or other suitable corrosion-resistant, biocompatible, electrically conductive material. The housing of an ICD is variously referred to as the "case", "casing", or "can". The term "can" will be used hereinthroughout for the sake of convenience.

Electromagnetic interference (EMI) coupled to the internal electronics of the ICD from external sources via the leads may interfere with the normal operation of the device and cause misoperation or malfunction thereof. Particular effects of EMI include confusing EMI for arrhythmias and consequential delivery of inappropriate therapy (e.g., spurious detection of an episode of fibrillation and consequential delivery of an inappropriate defibrillation shock), inadvertent temporary suspension of detection, possibly resulting in underdetection and non-treatment of actual arrhythmic episodes, inadvertent de-activation of the entire device, erroneous end-of-battery-life indications, inadvertent reset to power-up conditions and permanent damage to circuitry.

In general, because ICD sense amplifiers are much more sensitive than bradycardin pacemaker amplifiers, susceptibility of ICDs to EMI is much greater than the susceptibility of anti-bradycardia pacemakers to EMI. The larger size of the ICD can may also affect the coupling of external energy to the device. Patients are exposed to external EMI sources in the home, workplace, public places, and medical facilities. Exemplary EMI sources that are of concern include cellular phones, electronic anti-theft devices, radars, keyless (electronic) entry systems, and the like. In this regard, the Association for the Advancement of Medical Instrumentation (AAMI), pursuant to FDA Contract No. 223-74-5083, August 1975, has specified a voluntary EMI testing standard for pacemakers which has been widely adopted by both the pacemaker and ICD manufacturers as the de facto EMI testing standard to the present day. According to this standard, the pacemaker or ICD must be capable of normal operation when subjected to an EMI field having a frequency of 450 MHz, at a level of 200 V/m. If this test is passed, the operation of the device should not be adversely affected by EMI sources such as cellular phones, electronic anti-theft devices, radars, keyless (electronic) entry systems, and the like, which are commonly encountered.

Various techniques have been previously proposed in order to prevent EMI from being coupled to the internal circuitry of implantable cardiac stimulation devices. For example, special RF filters have been employed to filter out EMI, and looped wires have been utilized to cancel stray RF signals. For example, U.S. Pat. No. 4,934,366, issued to Truex et al., discloses a feedthrough connector for a pacemaker which includes a barrel assembly having overlapping conductive portions separated by non-conductive (insulating) portions which provide a capacitor structure which helps to filter out unwanted EMI from passing through the connector (leaking) into the interior of the pacemaker casing. However, the required structure is complex and difficult to fabricate, adds unwanted weight and volume to the device, and must be carefully designed for high-voltage (HV) applications, such as in ICDs, which deliver 750 V shocks.

U.S. Pat. No. 4,091,818, issued to Brownlee et al., discloses a pacemaker which includes a separate signal processing channel for detecting EMI and causing the pacemaker to revert to a safe operating rate in the presence of detected EMI which exceeds a predetermined threshold level. In addition to requiring additional complex circuitry, this technique compromises the efficaciousness of the pacemaker, since it requires that a prescribed safe pacing rate be employed in the presence of detected EMI. Thus, the ability of the device to deliver pacing pulses on demand at a different rate than the prescribed safe operating rate is inhibited. Moreover, the required circuitry is complex and adds to the manufacturing cost of the device, and further, adds unwanted weight and volume to the device.

U.S. Pat. No. 5,197,468, issued to Proctor et al., discloses a protective device for an implantable prosthesis, such as a pacer, which includes a ferrite body that is electrically and thermally connected to a lead wire and to ground, such as the housing of the internal electronics of the pacer. The protective device forms an inductor which blocks RF energy from reaching the internal electronics connected to the lead wire. The internal low frequency impedance of the ferrite body is high enough that the desired low frequency signals are not shunted to ground. The high frequency impedance of the inductor is high enough that the high frequency signals are effectively shunted to ground. In this manner, potential induced by the RF energy greater than the prescribed threshold frequency incident on the device "sees" an impedance to ground that is less than the impedance between the lead and the internal electronics, and any induced current flows preferentially to ground rather than to the internal electronics. Thus, the RF energy having a frequency greater than the prescribed threshold frequency is shunted to ground before it can reach the internal electronics connected to the lead wire. However, the required structure is complex and difficult to fabricate, adds unwanted weight and volume to the device, and may be unsafe for high-voltage (HV) applications, such as in ICDs, which deliver 750 V shocks.

Based on the above and foregoing, it can be readily appreciated that there presently exists a need in the art for an EMI shunt for an implantable medical device which overcomes the above-described drawbacks and shortcomings of the presently available technology. The present invention fulfills this need in the art.

SUMMARY OF THE INVENTION

The present invention encompasses a microstrip EMI shunt device for an implantable medical device (e.g., an ICD), which includes a microstrip transmission line positioned in a housing or can of the device, the microstrip transmission line having a first end which is electrically coupled to a connector wire of the device, and a second end which forms a microstrip circuit (open circuit stub) which uses the device can as a ground plane. In a disclosed embodiment, the microstrip circuit is formed by a copper circuit trace which is separated from the can by a thin dielectric layer. The microstrip transmission line has a length $n/4 \lambda$, where $\lambda$ is the wavelength of EMI having a frequency f which is desired to be shunted, where n is an odd integer $\geq 1$, and, where $f=v/\lambda$, and v represents the speed of propagation of the EMI in the microstrip medium. In operation, EMI of the frequency f is shunted via the microstrip transmission line prior to reaching the internal electronics of the device. Additional microstrip transmission lines having appropriately chosen lengths to shunt EMI of different frequencies can also be provided.

BRIEF DESCRIPTION OF THE DRAWINGS

These and various other features and advantages of the present invention will be more clearly understood from the following detailed description read in conjunction with the accompanying drawings, in which.

DETAILED DESCRIPTION OF THE INVENTION

Figure 1:
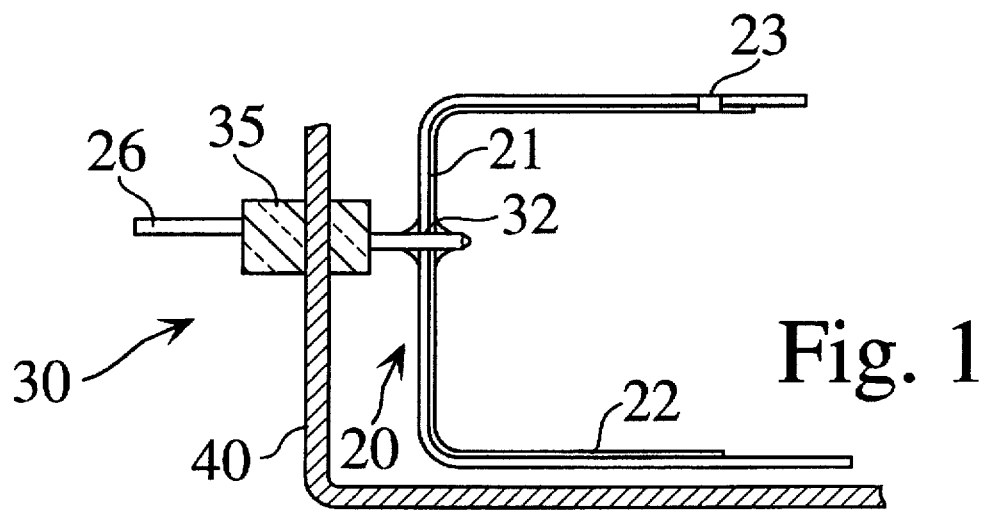
FIG. 1 is a fragmentary, cross-sectional view of an implantable cardioverter-defibrillator (ICD) having EMI microstrip shunts of the present invention incorporated therein.
Figure 2:
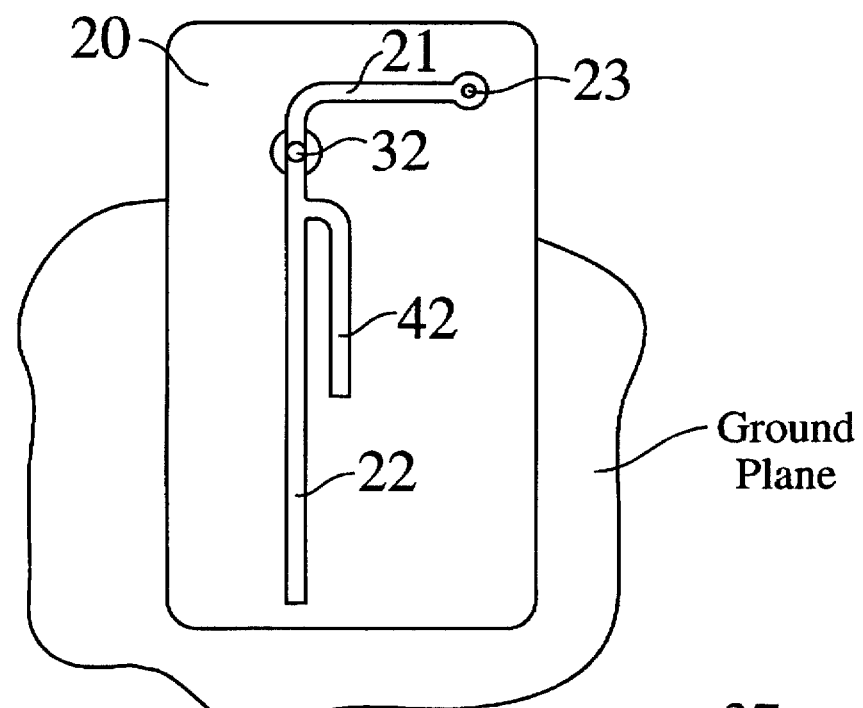
FIG. 2 is an isolation view of one of the EMI microstrip shunts depicted in FIG. 1.

With reference now to FIGS. 1 and 2, there can be seen a flex circuit 20 which includes a microstrip 22 electrically coupled to feedthrough or connector wire 26 of an implantable cardioverter-defibrillator (ICD) 30. Although the specific technique employed for attaching the microstrip 22 to the connector wire 26 is not limiting to the present invention, in a presently preferred embodiment, the connector wire 26 is inserted into through-hole 32 provided in the flex circuit 20, and soldered thereto. The flex circuit 20 can be easily manufactured using conventional flex circuit technology well within the realm of knowledge of those of ordinary skill in the pertinent art. The connector wire 26 can be terminated at the flex circuit 20, in which case, the electrical connection to the internal electronics (not shown) of the ICD 30 can be made by means of a conductor line (trace) 21 provided on the flex circuit 20 which ends at a terminal 23. Alternatively, the connector wire 26 can be directly connected to the internal electronics of the ICD 30 after passing through the through-hole 32. As can be seen, the connector wire 26 passes through a ceramic feedthrough 35 into the interior of the ICD housing or can 40, and then passes through the through-hole 32 where it is soldered in place. Conductor line 21 is connected to the internal electronics of the ICD from the through-hole 32. The proximal end of the microstrip 22 is soldered to the connector wire 26 and the distal end of the microstrip 22 forms an open-circuit stub. Only that portion of microstrip 22 which is in close proximity to and substantially parallel to the ground plane formed by a wall of can 40 functions as an EMI shunt.

The flex circuit is discussed with a single microstrip 22 (and a branch 42 in FIG. 2 discussed below) for purposes of illustration. In a preferred embodiment, a microstrip line is provided on flex circuit 20 for each individual sensing conductor which is fed through from outside to inside the ICD 30. Thus, for each of the two conductors in a bipolar sensing lead, a separate microstrip will be positioned on the flex circuit.

Figure 3:
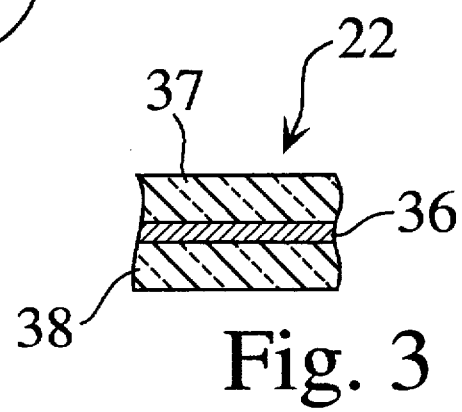
FIG. 3 is a cross-sectional view of the EMI microstrip shunts depicted in FIG. 1.

With additional reference now to FIG. 3, in a presently preferred embodiment of the invention microstrip 22 is constructed by sandwiching an electrically conductive, flexible strip 36, e.g., a strip of metal foil, such as copper foil, between first and second electrically insulating layers 37, 38, respectively, e.g., polyimide layers. The portion of flex circuit 20 containing microstrip 22 is preferably laid flush against an inside surface of the can 40 and secured thereto, e.g., by use of an adhesive such as epoxy, thus forming a microstrip transmission line, the distal end of which is open-circuited. In this regard, the flex circuit 20 can be flexed to conform to the contour of the interior surface of the can 40. However, it should be understood that the flex circuit 20 need not be secured to the interior surface of the can 40, as the flex circuit 20 may be positioned in the can 40 in any other suitable manner.

As will be readily appreciated by those skilled in the pertinent art, since the can 40 is in contact with the patient's body, it functions as an RF ground plane. However, any other ground plane can be used in lieu of the portion of the can 40 proximate the flex circuit 20, e.g., a separate metal layer (not shown) deposited on a multi-layer circuit board (not shown) of the ICD 20, and connected to ground.

The length of the microstrip 22 is chosen to be n/4 of the wavelength λ1 of the EMI which is desired to be shunted from the corresponding connector wire 26 before reaching the internal electronics (not shown) of the ICD 30, where n is an odd integer ≧1. In this manner, EMI whose wavelength is λ1, and whose frequency f1 is v/λ1 (where v represents the speed of propagation of the EMI in the microstrip medium), is shunted by the microstrip 22. In a presently contemplated embodiment of the present invention, the frequency of interest is 450 MHz and the microstrip medium is copper, and accordingly, a single microstrip having a length of approximately 3 inches is used. As previously discussed, this frequency is the one specified in the AAMI voluntary testing standard of August 1975. Suppression of frequencies near this frequency will ensure proper device operation during exposure to EMI from external sources such as cellular phones, radars, anti-theft devices, and the like, which are normally encountered by the patient.

It will be recognized by those skilled in the pertinent art that the microstrip 22 will appear as a low impedance to EMI having a frequency f1, so that EMI having a frequency near f1 (e.g., 450 MHz) will be shunted via the microstrip 22, and EMI having a frequency in an attenuation band (greater than 3dB of attenuation from 300 MHz to beyond 1.3 GHz) centered about the frequency f1 will be suppressed. Thus, the microstrip 22 functions as a λ/4 impedance transformer to transform the open-circuit at its distal end to an apparent short-circuit at its proximal end, and thus, the microstrip 22 will hereinafter be referred to as a microstrip EMI shunt 22.

As can be seen in FIG. 2, if it is also desired to shunt EMI having different frequencies, additional microstrips having appropriately chosen lengths can be additionally attached to the connector wire 26 such as the microstrips 42 which branches from the microstrips 22. The microstrips 22 and 42 can thus be considered individually to each constitute a separate microstrip EMI shunt, and collectively, can be considered to constitute a "microstrip EMI shunt device".

The microstrip EMI shunt device of the present invention does not require any additional circuit components and thus does not add any volume (and adds virtually no weight) to the ICD 30. Further, the microstrip EMI shunt device of the present invention is inherently safe for HV applications, and is easily manufacturable using well-known flex circuit fabrication technology. Moreover, the microstrip EMI shunt device of the present invention does not inhibit the normal operation of the internal electronics of the ICD in any manner, so long as the attenuation bands of the individual microstrip EMI shunts (typically hundreds of MHz) do not overlap the signal bandwidth of the internal electronics of the ICD (typically below 150 Hz).

Although a presently preferred embodiment of the present invention has been described in detail hereinabove, it should be clearly understood that many variations and/or modifications of the basic inventive concepts herein taught which may appear to those skilled in the pertinent art will still fall within the spirit and scope of the present invention as defined in the appended claims. In this connection, although the present invention has been described herein in connection with an implantable cardioverter-defibrillator, it will be readily apparent to those skilled in the pertinent art that the present invention will also have utility with respect to many other types of implantable medical devices.

What is claimed is:

1. A microstrip EMI shunt device for an implantable medical device which includes a housing, internal electronics contained within the housing, and a connector wire, the microstrip EMI shunt comprising:

a microstrip transmission line positioned in the housing, said microstrip transmission line having a first end electrically coupled to the connector wire and a second end which is open-circuited, wherein said connector wire is electrically coupled to said internal electronics;

wherein said microstrip transmission line has a length which is nλ/4, where λ represents the wavelength of EMI having a selected frequency f, and n is an odd integer >1; and, wherein said microstrip transmission line presents a low impedance to EMI having the frequency f, so that EMI of the selected frequency f is shunted prior to reaching the internal electronics of the implantable medical device.

2. The microstrip EMI shunt device as set forth in claim 1, wherein said housing is metallic and said microstrip transmission line is secured to an interior surface of the housing.

3. The microstrip EMI shunt device as set forth in claim 1, wherein the implantable medical device comprises an implantable cardiac stimulation device.

4. The microstrip EMI shunt device as set forth in claim 1, wherein the implantable cardiac stimulation device comprises an implantable cardioverter-defibrillator.

5. The microstrip EMI shunt device as set forth in claim 1, wherein said microstrip transmission line is comprised of an electrically conductive layer sandwiched between first and second electrically insulating layers.

6. The microstrip EMI shunt device as set forth in claim 5, wherein said electrically conductive layer is comprised of metal foil.

7. The microstrip EMI shunt device as set forth in claim 6, wherein each of said first and second electrically insulating layers is made of polyimide.

8. The microstrip EMI shunt device as set forth in claim 5, wherein each of said first and second electrically insulating layers is made of polyimide.

9. The microstrip EMI shunt device as set forth in claim 5, wherein said microstrip transmission line is laid flat on an interior surface of the housing and adhesively secured thereto.

10. The microstrip EMI shunt device as set forth in claim 1, wherein the implantable medical device further includes additional connector wires, and the microstrip EMI shunt device further comprises additional microstrip transmission lines each positioned in the housing, each of said additional microstrip transmission lines having a first end electrically coupled to a respective one of the additional connector wires, and a second end which is open-circuited, wherein each said connector wire is electrically coupled to said internal electronics.

11. The microstrip EMI shunt device as set forth in claim 10, wherein said additional microstrip transmission lines are secured to an interior surface of the housing.

12. The microstrip EMI shunt device as set forth in claim 10, wherein each of said additional microstrip transmission lines has a length which is nλ/4.

13. The microstrip EMI shunt device as set forth in claim 1, further comprising additional microstrip transmission lines each having a first end electrically coupled to the connector wire, and a second end which is open-circuited.

14. The microstrip EMI shunt device as set forth in claim 13, wherein each of said additional microstrip transmission lines has a different length.

15. The microstrip EMI shunt device as set forth in claim 13, wherein each of said additional microstrip transmission lines has a length appropriate to shunt EMI of a different respective frequency.

16. The microstrip EMI shunt device as set forth in claim 1, wherein the selected frequency f is equal to v/λ, where v represents the speed of the EMI in said microstrip transmission line.

17. The microstrip EMI shunt device as set forth in claim 1, wherein said housing is metallic and said microstrip transmission line is carried on a flex circuit with at least a major portion of said transmission line positioned substantially parallel to a wall of said housing.

* * * * *